(12) United States Patent
Witcher et al.

(10) Patent No.: US 6,566,090 B2
(45) Date of Patent: May 20, 2003

(54) RAPID READOUT STERILIZATION INDICATOR FOR LIQUID PERACETIC ACID STERILIZATION PROCEDURES

(75) Inventors: Kelvin J. Witcher, St. Paul, MN (US); Lewis P. Woodson, Apple Valley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/016,007

(22) Filed: Dec. 6, 2001

(65) Prior Publication Data

US 2002/0115131 A1 Aug. 22, 2002

Related U.S. Application Data

(62) Division of application No. 09/255,240, filed on Feb. 22, 1999, now Pat. No. 6,352,837.

(51) Int. Cl.[7] .................................................. C12Q 1/22
(52) U.S. Cl. ..................... 435/31; 435/287.4; 435/810
(58) Field of Search ........................... 435/31, 32, 176, 435/177, 180, 182, 287.4, 288.1, 288.7, 810; 422/57, 58, 61, 102

(56) References Cited

U.S. PATENT DOCUMENTS

| | | | |
|---|---|---|---|
| 4,407,960 A | 10/1983 | Tratnyek | 436/1 |
| 4,416,984 A | 11/1983 | Wheeler, Jr. | 435/31 |
| 4,443,538 A | 4/1984 | Cheetham | 435/41 |
| 4,448,548 A | 5/1984 | Foley | 374/160 |
| 4,461,837 A | 7/1984 | Karle et al. | 435/296 |
| 4,579,823 A | 4/1986 | Ryder | 435/296 |
| 4,596,773 A | 6/1986 | Wheeler, Jr. | 435/31 |

(List continued on next page.)

FOREIGN PATENT DOCUMENTS

| | | |
|---|---|---|
| EP | 0 939 200 | 11/1983 |
| EP | 0 152 898 A3 | 8/1985 |
| EP | 0 699 241 | 3/1996 |
| WO | WO 94/28164 | 12/1994 |
| WO | WO 95/06134 | 3/1995 |
| WO | WO 95/21936 | 8/1995 |
| WO | WO 96/06184 | 2/1996 |

OTHER PUBLICATIONS

JP abstract 05 049499 (1993).

"Experiments and Discussions on the Sterilization of Heat–sensitive Objects with Peracetic Acid", by Sprossig et al., Pharmazie 29(#2), 132–137 (1974).

"Studies on the Sterilizing Effect of Gaseous Peracetic Acid on Paper–packaged Materials", by Sprossing et al., Pharmazie 31(#7), 491–492 (1976).

(List continued on next page.)

Primary Examiner—David A. Redding
(74) Attorney, Agent, or Firm—John A. Burtis

(57) ABSTRACT

A sterilization indicator is useful for testing the effectiveness of sterilization procedures that disinfect objects by contacting them with a liquid sterilization procedure. The indicator includes an outer container having an open end and a cover material associated with the open end that is impermeable to liquids and bacteria. An enzyme-gel matrix is coated on a surface within the outer container that comprises a biologically inert polymeric gel and a source of an active enzyme dispersed within the gel. The enzyme has an activity that is correlated with the survival of at least one test microorganism that is commonly used to monitor the effectiveness of a sterilization procedure. A breakable ampoule within the outer container contains a substrate that is capable of reacting with any active enzyme remaining after the indicator has been subjected to a sterilization procedure to provide a detectable indication that the sterilization procedure was ineffective.

3 Claims, 4 Drawing Sheets

U.S. PATENT DOCUMENTS

| | | | |
|---|---|---|---|
| 4,659,700 A | 4/1987 | Jackson | 514/55 |
| 4,663,287 A | 5/1987 | Barker | 435/188 |
| 4,705,709 A | 11/1987 | Vailancourt | 428/36 |
| 4,717,661 A | 1/1988 | McCormick et al. | 435/31 |
| 4,731,222 A | 3/1988 | Kralovic et al. | 422/37 |
| 4,741,437 A | 5/1988 | Gorski et al. | 206/222 |
| 4,743,537 A | 5/1988 | McCormick et al. | 435/296 |
| 4,828,797 A | 5/1989 | Zwarun et al. | 422/55 |
| 4,835,003 A | 5/1989 | Becker et al. | 427/2 |
| 4,885,253 A | 12/1989 | Kralovic | 435/296 |
| 4,892,706 A | 1/1990 | Kralovic et al. | 422/28 |
| 4,918,003 A | 4/1990 | Macaro et al. | 435/31 |
| 4,925,668 A | 5/1990 | Khan et al. | 424/422 |
| 4,937,115 A | 6/1990 | Leatherman | 428/36.4 |
| 5,073,488 A | 12/1991 | Matner et al. | 435/31 |
| 5,077,008 A | 12/1991 | Kralovic et al. | 422/37 |
| 5,116,575 A | 5/1992 | Badertscher et al. | 422/28 |
| 5,132,211 A | 7/1992 | Lundin et al. | 435/31 |
| 5,167,923 A | 12/1992 | Van Iperen | 422/58 |
| 5,209,909 A | 5/1993 | Siegel et al. | 422/292 |
| 5,217,698 A | 6/1993 | Siegel et al. | 422/295 |
| 5,225,160 A | 7/1993 | Sanford et al. | 422/28 |
| 5,349,654 A | 9/1994 | Bond et al. | 422/292 |
| 5,350,563 A | 9/1994 | Kralovic et al. | 422/28 |
| 5,391,360 A | 2/1995 | Kochte et al. | 422/292 |
| 5,407,685 A | 4/1995 | Malchesky et al. | 424/449 |
| 5,451,372 A | 9/1995 | Larsson et al. | 422/58 |
| 5,498,526 A | 3/1996 | Caputo et al. | 435/31 |
| 5,508,046 A | 4/1996 | Cosentino et al. | 424/616 |
| 5,516,648 A | 5/1996 | Malchesky et al. | 435/31 |
| 5,518,927 A | 5/1996 | Malchesky et al. | 436/1 |
| 5,552,320 A | 9/1996 | Smith | 435/287.4 |
| 5,620,656 A | 4/1997 | Wensky et al. | 422/28 |
| 5,736,355 A | 4/1998 | Dyke et al. | 435/31 |
| 5,739,004 A | 4/1998 | Woodson | 435/31 |
| 5,770,393 A | 6/1998 | Dalmasso et al. | 435/31 |
| 5,801,010 A | 9/1998 | Falkowski et al. | 435/31 |
| 5,833,935 A | 11/1998 | Malchesky | 422/300 |
| 6,352,837 B1 * | 3/2002 | Witcher et al. | 435/31 |

OTHER PUBLICATIONS

"Interaction between Formaldehyde–Perserved Implantates and Peracetic Acid", by Wenzel et al., Pharmazie 37(#3), 1982.

"Peracetic Acid as Disinfectant—A Review", by Flemming, Zbl. Bakt. Hyg. 1 Abt. Orig B. 179, 97–111 (1984).

"Foundation of Disinfection" by Horn et al., Handbook of Disinfection and Sterilization, vol. I, pp. 173–177.

"Suitability of Peracetic Acid for Sterilization of Media for Mycoplasma Cultures", by Wutzler et al., Journal of Clinical Microbiology, vol. 1, No. 3, Mar. 1975, pp. 246–249.

"A Flash Sterilizer Using Peracetic Acid", by Crawford, Jr., U.S. Army Medical Bioengineering Research and Development Laboratory, Jul. 1976.

"Peracetic Acid Aerosols", by Greenspan, Proc. $42^{nd}$ Ann. Meet. Chem. Specialities Manufact. Assoc., 1955, pp. 59–64.

"Halophilic Bacteria Susceptibility to Peracetic Acid Vapor and Ethylene Oxide", by Tasch et al., Applied Microbiology, vol. 25, No. 2, Feb. 1973, pp. 205–207.

"Sporicidal Effect of Peracetic Acid Vapor", by Portner et al., Applied Microbiology, vol. 16, Nov. 1968, pp. 1782–1785.

"Aldehyde–agarose gels as activated supports for immobilization–stabilization of enzymes", by Guisan, Enzyme Microb. Technol., Jun. 1988, vol. 10, pp. 375–382.

"Immobilization–Stabilization of Penicillin G Acylase from *Escherichia Coli*", by Alvaro et al., Applied Biochemistry and Biotechnology, 1989, pp. 181–195.

"An Enzyme–Polymer Film Prepared with the Use of poly –(Vinyl Alcohol) Bearing Photosensitive Aromatic Azido Groups", by Miyairi, Biochim. Biophys. Acta., 1979, vol. 571, pp. 374–377.

* cited by examiner

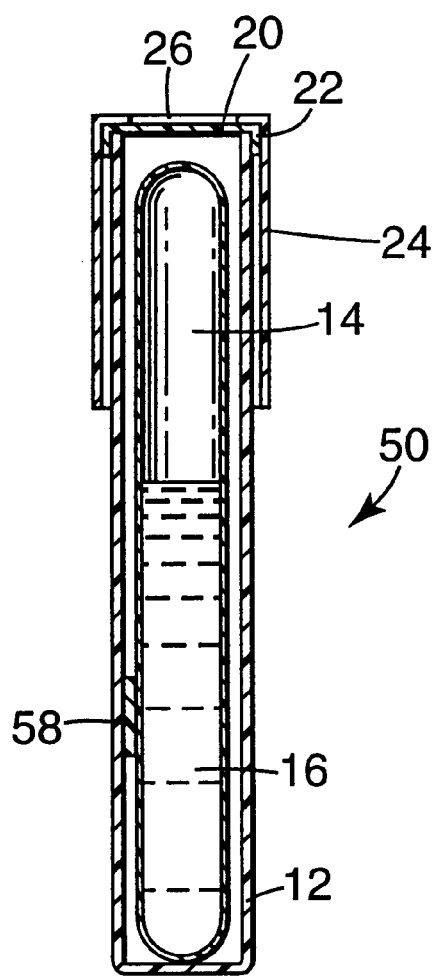
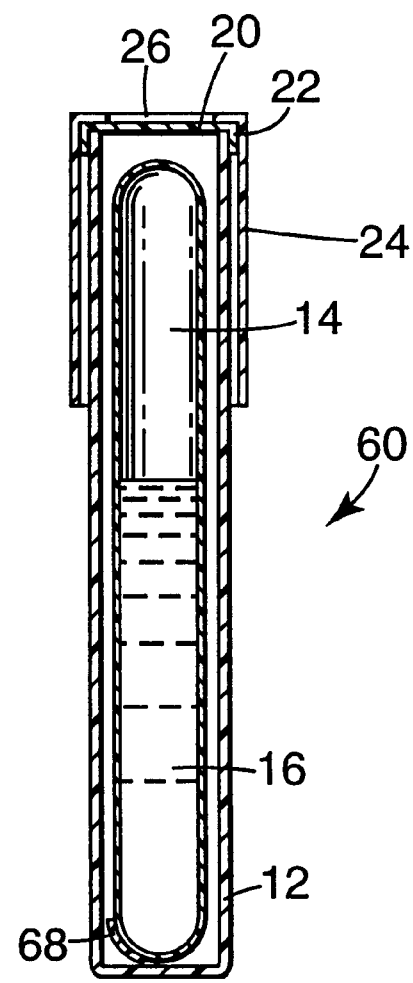
Fig. 5          Fig. 6

RAPID READOUT STERILIZATION INDICATOR FOR LIQUID PERACETIC ACID STERILIZATION PROCEDURES

CROSS-REFERENCE TO OTHER APPLICATIONS

This application is a divisional of U.S. application Ser. No. 09/255,240 filed Feb. 22, 1999, now U.S. Pat. No. 6,352,837.

FIELD OF THE INVENTION

This invention relates to sterilization indicators for use in monitoring the effectiveness of sterilization procedures that use liquid sterilants, and in particular to sterilization indicators for use in monitoring the effectiveness of sterilization procedures that use liquid peracetic acid as a sterilant.

BACKGROUND OF THE INVENTION

In hospitals, industry and research it is necessary to sterilize certain articles, such as glassware, medical instruments and the like, to ensure that they are completely free of contamination by microorganisms that are capable of causing infection and disease. For example, it is well known that surgical instruments must be sterilized before they may be used in a surgical operation. Articles are sterilized by placing them in a machine called a sterilizer and subjecting them to a sterilization procedure of a type that is generally recognized as being effective at killing microorganisms.

Many different types of sterilization procedures are known in the art. These procedures may be differentiated from each other based on the identity of the sterilant used in each to destroy contaminating microorganisms. Currently, the most widely used procedures employ steam or an antimicrobial gas as sterilants.

However, sterilization procedures have recently been developed that use liquid sterilants. In particular, sterilization procedures that use liquid peracetic acid as a sterilant have become increasingly popular of late because they may be used to sterilize articles that cannot withstand the high temperatures and pressures of steam sterilization. A liquid peracetic acid sterilization procedure is described in U.S. Pat. No. 5,077,008 (Kralovic).

Sterilization indicators are quality control devices that are included with every load of articles placed in a sterilizer to monitor the antimicrobial effectiveness of each procedure conducted by the sterilizer. The indicators determine whether or not a sterilization procedure was lethal to contaminating microorganisms in the load. Typically, in the event of sterilization failure the indicators provide a readily detectable signal—such as fluorescence, luminescence or a color change—indicating that contaminating microorganisms may have survived and that the articles in the load must be subjected to another sterilization cycle.

Sterilization indicators have been developed that are both rapid and accurate for monitoring steam and gas procedures. But until now, a critical shortcoming associated with the use of liquid sterilant procedures has been that sterilization indicators have not been available that meet the performance standards set for sterilization indicators used with steam or gas procedures. In general, sterilization indicators for use with liquid sterilants are neither as fast or as dependable as sterilization indicators developed for use with steam.

Effective sterilization indicators that are widely used to monitor steam and gas sterilization procedures include biological indicators, rapid readout biological indicators, and dual rapid readout biological indicators. With each of these types of sterilization indicators, the failure of a sterilization procedure is indicated by a detectable change in a biological specimen—either an enzyme, a microorganism or both—that is attached to a carrier substrate, such as filter paper. In theory all of these sterilization indicators should be just as effective with liquid sterilants as they are with steam or gas. However, in practice it is often the case that the biological specimen is washed off of the carrier material during the procedure, or the carrier material is degraded by the liquid sterilant, so that any results obtained are unreliable.

Biological indicators have heretofore been recognized in the art as providing an accurate and direct method for determining whether or not a sterilization procedure has been effective, for steam and gas. Biological indicators are sterilization indicators that monitor the effectiveness of a sterilization procedure by measuring the effect of the procedure on a population of test microorganisms included in the indicator. If a sterilization procedure fails to generate a condition in the sterilizer that is lethal to the test microorganisms, surviving cells are detectable following a period of incubation and growth.

The test microorganism used in a biological indicator is typically a microorganism that is several times more resistant to the sterilization procedure being monitored than any microorganism that would likely to be present due to natural contamination. Spores of a microorganism, such as a bacterium, fungus, or protozoan, are most commonly used as the test microorganisms in biological indicators because of their hardy resistance to sterilization procedures. *Bacillus stearothermpophilus* spores are preferred for use in biological indicators for monitoring steam sterilization procedures, while *Bacillus subtilis* spores are preferred for use in biological indicators for ethylene oxide gas procedures.

Many biological indicators currently in use are self-contained biological indicators, which include both a spore strip and growth medium in separate compartments within the same closed container. During a sterilization procedure, sterilant, either steam or gas, enters the container through a shielded vent and contacts the spores but does not contact the growth medium. The barrier between the separate compartments is then broken, and the growth medium and spores are combined and incubated. Typically, a pH indicator compound that changes color in response to spore outgrowth is included with the growth medium. If test spores survive the sterilization procedure and grow out during incubation, the growth medium changes color, providing a readily detectable signal that the sterilization procedure has failed. A major advantage of self-contained biological indicators is that they can be sterilized, incubated and read without ever opening the container and exposing its contents to potential contamination from microorganisms present in the environmental air.

A typical self-contained biological indicator is described in U.S. Pat. No. 3,661,717 (Nelson). The indicator includes a compressible outer tube having one open end, and a porous, protective material covering the open end that allows sterilant, but not bacteria, to enter and leave the tube. A sealed glass ampoule within the outer tube contains growth medium and a chemical compound that changes color in response to spore growth. The outer tube also contains a spore strip between the outer tube and the ampoule. During a sterilization procedure steam or gas sterilant enters the indicator through the cover material and contacts the spores on the spore strip. The glass ampoule is then crushed by squeezing the compressible walls of the outer tube, and the spores are combined with the growth media. The indicator is incubated for a prescribed period of time and observed for a color change indicating spore growth and sterilization failure.

Attempts have been made in the art to develop biological indicators that are suitable for use with liquid sterilants. U.S. Pat. No. 4,885,253 (Kralovic) discloses a biological indicator for use with liquid sterilants that includes a vial with a sealed compartment containing growth media and a vented cap that is capable of being moved from an open position in which sterilant may freely enter the vial to a closed position. A spore strip is disposed above the sealed compartment and is exposed to sterilant during the sterilization procedure. Afterwards, a cutter device attached to the inner surface of the cap severs the barrier separating the growth media from the rest of the compartment, causing the spore strip to drop into the growth media for incubation.

U.S. Pat. No. 5,736,355 (Dyke) discloses a biological indicator for use with liquid sterilants that includes a vial with a sealed compartment containing growth medium and a vented cap that moves from an open position in which sterilant can freely enter the container to a closed position. A dart with an attached spore strip is attached to the cap for puncturing the seal and immersing the spore strip in the culture medium for incubation. The spore strip is covered by a microporous membrane that is said to prevent the spores from being washed away by liquid sterilant during a sterilization procedure.

U.S. Pat. No. 5,516,648 (Malchesky) discloses a biological indicator for use with liquid sterilants that includes a spore strip encapsulated in a microporous, hydrophylic membrane that is permeable to sterilant but impermeable to spores. The encapsulated spore strip is located above a sealed media compartment in a vial, and is exposed to sterilant during a sterilization procedure. It is said that the microporous membrane prevents spores from being washed off the spore strip by sterilant. The vial includes a cap with a cutting device for rupturing the seal after a sterilization procedure in order to drop the encapsulated spore strip into the growth media.

Although biological indicators are accurate, they are slow and may require up to seven days to give a final result. Ideally, articles that have been exposed to a sterilization procedure should be quarantined until biological indicator results have confirmed that the procedure was effective. However, as a practical matter this is rarely done. Limitations on storage space and the constant need for freshly sterilized supplies make it difficult, if not impossible, to hold goods in reserve inventory for the long period of time necessary for biological indicators to provide a result. Instead, ostensibly sterilized goods are often put to immediate use, and later-obtained negative biological indicator results are used to identify and remedy existing sterility problems, rather than to prevent them from occurring in the first instance.

Rapid readout biological indicators have been developed that avoid these problems by combining the accuracy of biological indicators with the speed necessary for medicine and industry. These indicators rely on an enzyme-substrate reaction that provides a detectable indication of sterilization accuracy within hours or minutes, rather than days as required with conventional biological indicators.

Rapid readout biological indicators are described in U.S. Pat. Nos. 5,073,488 (Matner et al.), 5,418,167 (Matner et al.), and 5,223,401 (Foltz et al.), which are incorporated herein by reference. These indicators have a self-contained design that includes an enzyme and a substrate that is capable of reacting with the enzyme, in separate compartments within the same container. In a preferred design, the indicators include a compressible outer tube with one open end and a porous, protective cover membrane over the open end that is permeable to sterilant but impermeable to bacteria. A sealed glass ampoule within the outer container contains a substrate solution. A carrier strip made of filter paper or some other appropriate material is located between the walls of the outer tube and the ampoule, and includes on its surface a source of an active enzyme having an enzyme activity that is correlated with the survival of a test microorganism that is commonly used in biological indicators to monitor sterilization procedures. During a sterilization procedure, sterilant enters the outer tube and contacts the enzyme located on the carrier strip. The inner ampoule is then crushed, and the enzyme and substrate are combined and incubated. If any of enzyme on the carrier remains active after the sterilization procedure, it will react with the substrate to form an enzyme-modified product that is detectable as luminescence, fluorescence or a color change, indicating sterilization failure.

Dual rapid readout biological indicators are rapid readout indicators that measure the effectiveness of a sterilization procedure with both a rapid enzyme-substrate reaction and a confirmatory spore outgrowth test of the type used in conventional biological indicators. 3M ATTEST™ 1292 Rapid Readout Indicators, available from 3M Company, St. Paul, Minn., for use in monitoring steam sterilization procedures, are dual rapid readout indicators in which *Bacillus stearothermophilus* spores serve as both the source of active enzyme for the enzyme test and the test microorganism for the confirmatory outgrowth test. The spores are coated on the surface of a carrier strip that is located between the walls of a compressible outer tube and a sealed glass ampoule containing growth medium and substrate. After sterilization the glass ampoule is crushed by squeezing the outer tube, and the spores and the contents of the ampoule are combined and incubated. The indicator is examined for fluorescence, indicating sterilization failure, after 3 hours using a 3M ATTEST™ Model 190 Rapid Autoreader, and then is incubated for a full 7 days for the confirmatory spore outgrowth test.

Although rapid readout sterilization indicators and dual rapid readout sterilization indicators are highly accurate, it has not previously been possible to use them with liquid sterilants, because of the tendency of the sterilant to wash the source of enzyme from the indicators. It is therefore an object of the present invention to provide rapid readout biological indicators and dual rapid readout indicators that overcome this problem and that may be used to accurately and reliably monitor a sterilization procedure that employs a liquid sterilant.

SUMMARY OF THE INVENTION

The invention provides a rapid readout biological indicator that may reliably be used to monitor sterilization procedures that disinfect articles with liquid sterilants, including liquid peracetic acid. The indicator relies upon an enzyme-substrate reaction to provide a rapid indication of whether or not a sterilization procedure has been effective. The invention overcomes the known tendency of liquid sterilants to wash biological test specimens out of biological indicators, rendering them unreliable, by providing the biological test specimen of the indicator in a protective gel matrix coated on a surface within the indicator housing. Sterilant may enter the matrix and contact the biological test material, but the biological material remains enmeshed in the matrix and is not washed away by the sterilant.

The indicator of the invention includes a compressible outer container having one open end that is shielded by a cover membrane that is permeable to liquids but impermeable to bacteria. An enzyme-gel matrix is coated on a surface within the outer container. The enzyme-gel matrix includes a source of active enzyme dispersed within a water-insoluble, biologically inert gel. A breakable sealed ampoule within the outer container contains a substrate that is capable of reacting with the active enzyme in the enzyme-gel matrix. During a sterilization procedure, sterilant enters the outer tube through the cover membrane and contacts the source of active enzyme in the enzyme-gel matrix. The substrate ampoule is then broken by compressing the outer tube, and the substrate and enzyme-gel matrix are combined and incubated. If the sterilization procedure is ineffective, active enzyme will react with substrate to form a product that provides a detectable indication that the sterilization procedure has failed and must be repeated.

The enzyme-gel matrix has physical properties such that during a sterilization procedure, sterilant may enter the matrix and contact the source of active enzyme without washing the source of active enzyme out of the indicator. The enzyme used in the indicator has an enzyme activity that is correlated with the survival of at least one test microorganism that is commonly used to monitor the effectiveness of a sterilization procedure. The enzyme is substantially inactivated by a sterilization procedure that is lethal to the test microorganism, but is not substantially inactivated by a sterilization procedure that is not lethal to the test microorganism.

The source of active enzyme used in the indicator of the invention may be a purified enzyme, a microorganism or both. If a microorganism is used as the source of active enzyme, the indicator may be a dual rapid readout biological indicator in which the microorganism serves as both the source of active enzyme for the rapid enzyme test and the microorganism for the outgrowth test. A growth medium is included in the substrate ampoule in the dual rapid readout biological indicator to facilitate growth of any surviving spores after exposure to a sterilization procedure.

In an embodiment of the indicator that is suitable for monitoring liquid peracetic acid sterilization procedures, the source of active enzyme is *Bacillus stearothermophilus* spores.

The enzyme-gel matrix in the indicator of the invention may be coated on any surface within the outer tube that is exposed to sterilant during a sterilization procedure. For example, it may be coated on the interior surface of the outer tube, on the exterior surfaces of the substrate ampoule, or on a carrier material such as filter paper or a glass bead.

BRIEF DESCRIPTION OF THE FIGURES

FIG. 5 is a cross-sectional view of an alternative embodiment of the sterilization indicator of the invention.

FIG. 6 is a cross-sectional view of an alternative embodiment of the sterilization indicator of the invention.

DETAILED DESCRIPTION OF THE INVENTION

Figure 1:
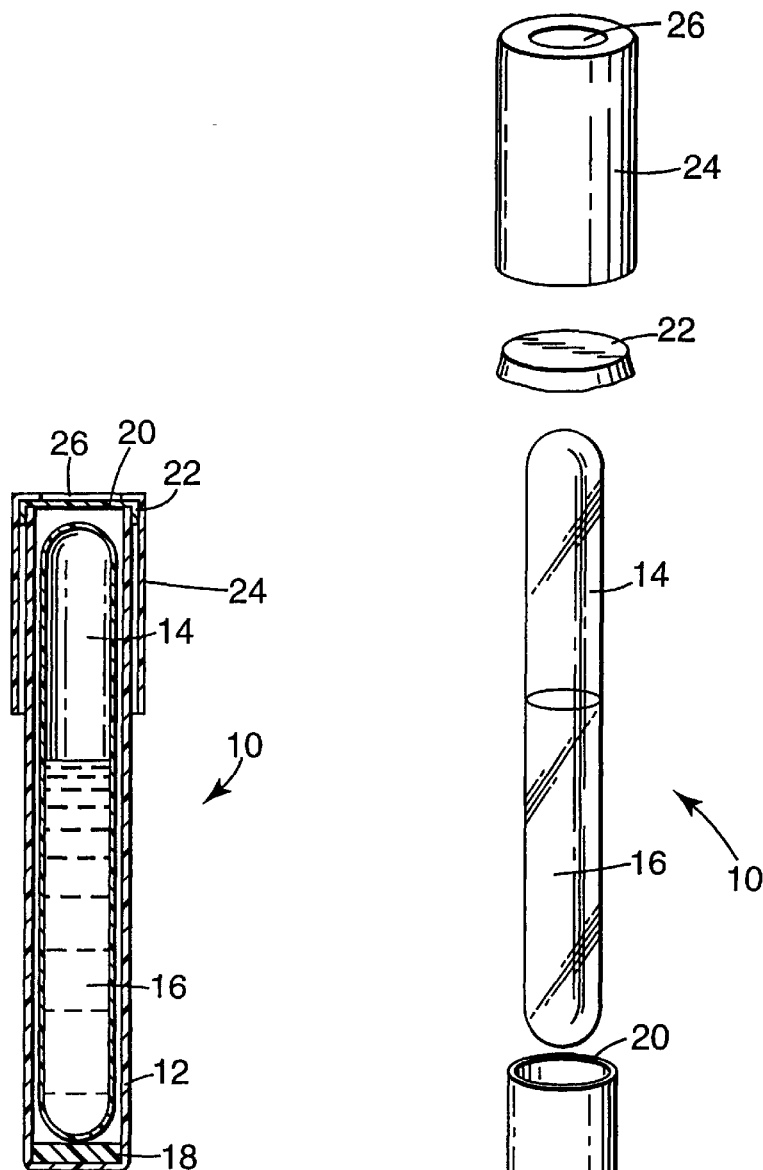
FIG. 1 is a cross-sectional view of an embodiment of the sterilization indicator of the invention.

The invention provides rapid readout biological indicators and dual rapid readout biological indicators that are suitable for use in monitoring sterilization procedures that use liquid sterilants. The indicators rely upon an enzyme-substrate reaction to provide a rapid and accurate determination of whether a particular sterilization procedure was effective. A source of active enzyme and a substrate capable of reacting with the active enzyme are included in the indicator, in separate compartments. During a sterilization procedure the source of active enzyme is exposed to a sterilant, which, if the procedure is effective, should inactivate the enzyme. The enzyme and substrate are then combined and incubated. If any of the enzyme in the indicator remains active following the procedure, it will react with the substrate to form an enzyme-modified product that provides a detectable indication that the sterilization procedure has failed. The detectable indication may be fluorescence, luminescence, a color change or radiation.

The source of active enzyme in the indicators of the invention is included as part of an enzyme-gel matrix that allows liquid sterilant to contact the source of active enzyme without washing it out of the indicator, as was previously known to occur with liquid sterilant procedures.

The source of active enzyme used in the indicator may be either a purified enzyme, a microorganism that expresses active enzyme or both. The active enzyme itself, which reacts with the substrate, is an enzyme that has an activity that is correlated with the survival of at least one test microorganism that is commonly used in biological indicators to monitor the effectiveness of sterilization procedures. Preferably, the enzyme is one that is not inactivated until at least shortly after the death of the test microorganism with which its activity is correlated.

Enzymes and substrates that are suitable for use in the rapid readout biological indicators and dual rapid readout biological indicators of the invention are identified in U.S. Pat. Nos. 5,073,488 (Matner et al), 5,418,167 (Matner et al.), and 5,223,401 (Foltz et al.), which are incorporated herein by reference for all they disclose.

Suitable enzymes include enzymes derived from spore-forming microorganisms, such as *Bacillus stearothermophilus* and *Bacillus subtilis*. Enzymes from spore-forming microorganisms that are useful in the biological indicators of the invention include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-B-glucosaminodase, beta-D-cellobiosidase, alanine aminopeptidase, proline aminopeptidase and fatty acid esterases.

Chromogenic and fluorogenic substrates that react with enzymes to form detectable products, and that are suitable for use in the sterilization indicator of the invention, are well known in the art. (M. Roth, *Methods of Biochemical Analysis*, Vol. 17, D. Block, Ed., Interscience Publishers, New York, 1969, p. 89, incorporated herein by reference; S. Udenfriend, *Fluorescence Assay in Biology and Medicine*, Academic Press, New York, 1962, p. 312, incorporated herein by reference; and D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174, incorporated herein by reference). These substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound, or compounds, to generate a color or fluorescent signal.

In the preferred embodiment of the invention, the source of active enzyme in the indicator is the spore of a microorganism. Microorganisms that are particularly preferred to serve as the source of active enzyme include *Bacillus stearothermophilus* and *Bacillus subtilis* spores, which are microorganisms that are commonly used as test microorganisms in spore outgrowth biological indicators utilized to monitor sterilization procedures. Where dual rapid readout indicators are used, these microorganism may serve as both the source of active enzyme in the rapid enzyme test and the test microorganism for the spore outgrowth test.

In the most preferred embodiment of the indicator, which is suitable for monitoring sterilization procedures that utilize liquid sterilants, including liquid peracetic acid, the source of active enzyme is *Bacillus stearothermophilus* spores and the substrate is 4-methylumbelliferyl-alpha-D-glucoside, which reacts with the enzyme alpha-D-glucosidase expressed by *Bacillus stearothermophilus*.

Figure 2:
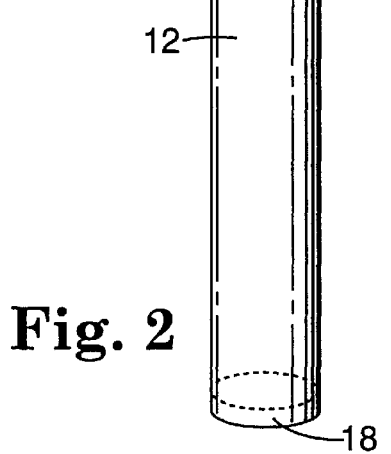
FIG. 2 is an exploded view of the sterilization indicator shown in FIG. 1.

Turning now to the figures, FIGS. 1–2 show an indicator 10 that may be used to monitor liquid sterilization procedures. The indicator 10 includes an outer container 12 made of a compressible plastic material having one open end 20. A protective cover membrane 22 associated with the open end 20 is permeable to liquids but impermeable to bacteria. A vented cap 24 made of a rigid plastic material holds the cover membrane 22 firmly in place on the outer tube 12. A sealed, breakable ampoule 14 within the outer container 12 contains a substrate solution 16 that is capable of reacting with a source of active enzyme to provide a detectable signal in the event of the failure of a sterilization procedure. An enzyme-gel matrix 18, including a source of active enzyme, is coated on a surface within the outer container 12 that is exposed to contact with sterilant during a sterilization procedure.

The indicator 10 is placed in a sterilizer with a load of articles and exposed to a sterilization procedure. During the procedure, liquid sterilant enters the outer container 12 through portal 26 and passes through the protective cover membrane 22. The sterilant then contacts the enzyme-gel matrix 18 and interacts with the enzyme dispersed throughout the matrix. The enzyme-gel matrix 18 is permeable to liquid sterilant, so that the sterilant may contact the active enzyme during the sterilization procedure. However, the gel securely retains the enzyme source and prevents it from being washed away by the sterilants.

After exposure to liquid sterilant, the indicator 10 is washed with water to remove any residual sterilant. The ampoule 14 is then crushed by compressing or squeezing the outer container 12, and the substrate solution 16 is combined with the enzyme-gel matrix 18 in the outer tube 12 and incubated for a period of time sufficient for the substrate to react with the enzyme. If the sterilization procedure is effective, all of the enzyme in the enzyme-gel matrix 18 will be inactivated and no reaction between the enzyme and the substrate will occur. However, if active enzyme survives the sterilization procedure, it will react with the substrate to form an enzyme-substrate product that provides a detectable indication that the sterilization procedure has failed and must be repeated.

The outer container 12 is preferably made of a deformable plastic material that can be readily compressed by the human hand. It is desirable that the plastic material be translucent or transparent, so that a detectable indication of sterilization failure, such as fluorescence or a color change, can be observed through the walls of the container 12. The plastic material of the outer container 12 should also be substantially impermeable to bacteria, liquids and gases and should not retain significant levels of residual liquid sterilant following a sterilization procedure and washing. As used herein, "a significant level of residual liquid sterilant" means a level that would interfere with the accuracy of the sterilization indicator by inactivating enzyme in the indicator when the sterilization indicator has failed to kill microorganisms in the indicator.

Suitable plastic materials for use in the outer container 12 include, for example, polypropylene, polycarbonates, polyamides, polymethylpentenes and polyesters. In the most preferred embodiment of the invention, the outer container 12 is made of polypropylene. The outer container 12 may be made in any size that is convenient given the size of the sterilizer and the space available for the indicator within it, but should not be so large that it is unwieldy to use or so small that the indicator cannot be easily manipulated by hand. In a preferred embodiment, the outer container 12 is about 5 cm in length and has an outer diameter of about 0.65 cm.

The cap 24 of the indicator 10 is preferably made of the same material as the outer container 12. The portal 26 is most preferably located on the top of the cap 24, directly over the cover membrane 22. However, the location of the portal 26 is not critical, and portal 26 may alternatively be placed on the sides of the cap 24. In addition, the number of portals 26 may be varied without deviating from the scope of the invention, and two or more portals 26 may be used instead of one. In a preferred embodiment, two or three portals 26 are spaced along the sides of the cap 24.

The protective cover membrane 22 is preferably made of a fibrous material that is wettable, absorbent, and resistant to degradation by liquid sterilants such as peracetic acid. The material of the cover membrane 22 should also be microporous, such that it is permeable to liquid sterilants and gases but impermeable to microorganisms, such as bacteria, fungi, and protozoa. Preferably, the cover membrane 22 should have pores that are no larger than 0.45 microns.

Suitable materials for cover membrane 22 include fibrous materials such as cotton, cloth, glass fibers, glass wool, glass, nonwoven webs of natural or synthetic polymers or copolymers, filter papers, microporous hydrophobic and hydrophilic films, open celled polymeric foams, semipermeable plastic films, polytetrafluoroethylene (PTFE), and nonwoven webs coated with polyglycerol fatty acid derivatives. Nonwoven materials that are suitable for use in the cover membrane 12 include nonwoven webs made of rayon, polypropylene, polyester, rayon/polypropylene, cellulosics, cellulosic/synthetic fiber blends, nylon or other natural or synthetic polymers and copolymers.

The cover membrane 22 of the indicator is preferably made of a nonwoven web of a hydrophilic polymer or copolymer, or a blend of cellulosic and synthetic fibers. A particularly preferred material is a nonwoven web of hydrophilic rayon/polypropylene.

Where the cover membrane 22 is a nonwoven material that has been coated with a polyglycerol fatty acid derivative, the nonwoven material is preferably polypropylene and the polyglycerol fatty acid derivative is selected from the group consisting of decaglycerol monostearate, hexaglyceryl polyricinolate, decaglycerol pentaoleate, tetraglycerol monooleate, polyaldo 10-6-0 K-PG decaglycerol hexaoleate, and polyaldo DGDO K-FG decaglyceryl decaoleate, or mixtures of two or members of the group.

The ampoule 14 of the indicator 10 is made of a breakable material, such as glass or some other material that is capable of being crushed when the outer container 12 is compressed. The ampoule 14 contains a solution 16 that includes a substrate. In an alternative embodiment for use in dual rapid readout indicators, the ampoule may contain both a substrate and a spore growth medium. In this embodiment, the substrate is capable of reacting with active enzyme in the spores in the dual indicator for the rapid enzyme test, and the growth medium promotes the growth of spores in the spore outgrowth portion of the test.

The enzyme-gel matrix 18 includes a biologically inert polymeric gel and a source of active enzyme dispersed within the gel. The source of active enzyme may be a purified enzyme, a microorganism or both, but is preferably a microorganism and most preferably microorganism spores. In a particularly preferred embodiment, suitable for use in monitoring liquid peracetic acid sterilization procedure, the source of active enzyme is *Bacillus stearothermophilus* spores.

The biologically inert polymeric gel selected for used in the enzyme-gel matrix may be any polymeric gel that is insoluble in both water and the liquid sterilant used in the sterilization procedure to be monitored with the sterilization indicator 10. Suitable gel materials include copolymers of polyoxyethylene and polyoxypropylene, and polymers and copolymers of polyvinylpyrolidone, polyacrylamide, hydroxmethylacrylate-tetradecaethylene glycol, polyvinyl alcohol, polyelectrolyte complex-stabilized calcium alginate and chitosan, polyacrylamide hydrazide, collagen, kappa-carrageenan, polyurethane, polyurethane ureas, siloxane urethanes, polyglutaraldehyde, hyaluronic acid and polyethyleneimine, and any of the polymeric gels disclosed in U.S. Pat. No. 5,739,004 (Woodson), which is incorporated herein by reference.

Preferably, the polymeric gel is a copolymer of polyvinylpyrolidone selected from the group that includes polyvinylpyrolidone/polycarbamyl polyglycol esters, such as those available as PECOGEL™ A-12 PECOGEL™ H-12, PECOGEL H-115 and PECOGEL™ H-1220, from Phoenix Chemical, Inc., Somerville, N.J.; polyvinylpyrolidone/dimethylaminoethylmethacrylate/polycarbamyl polyglycol esters, such as those available as PEGOGEL™ GC-310 and PECOGEL™ GC-1110, from Phoenix Chemical, Inc.; as PECOGEL; and polyvinylpyrolidone/dimethiconylacrylate/polycarbamyl/polyglycol esters, such as those available as PECOGEL™ S-1120, from Phoenix Chemical, Inc. In the most preferred embodiment, the polymeric gel is a polyvinylpyrolidone/polycarbamyl polyglycol ester.

The enzyme-gel matrix is prepared by suspending the source of active enzyme, either purified enzyme or spores, in the polymeric gel at a preselected concentration. In the preferred embodiment, *Bacillus stearothermophilus* spores are washed and centrifuged into a pellet, then suspended in the polymeric gel material at a concentration in the range of about $1 \times 10^6$ to $1 \times 10^{10}$ spores per milliliter, and more preferably in the range of about $1 \times 10^7$ to $1 \times 10^9$ cells per milliliter. A pre-determined number of spores is then coated on a surface in the indicator. The number of spores coated in each indicator is preferably in the range of about $10^2 14\ 10^8$ spores, and more preferably is about $10^6$ spores. However, the number of spores needed in each indicator will vary depending on the procedure to be monitored, and the optimal number for a particular use may be readily determined by one of ordinary skill without undue experimentation The enzyme-gel matrix 18 may be coated on any surface within the outer container 12 that will be exposed to liquid sterilant during a sterilization procedure. Suitable surfaces include the inner walls or end of the outer container 12 and the outer walls of the ampoule 14. Alternatively, the enzyme-gel matrix may be coated onto a substrate, such as filter paper or a glass bead, which can be placed within the outer container. The figures illustrate several variations on the placement of the enzyme-gel matrix in the indicator.

FIGS. 1–2 shows an embodiment of the indicator 10 in which the enzyme-gel matrix 18 is coated on the interior of the closed end of the outer container 12. This placement of the enzyme-gel matrix is highly desirable because it is directly beneath the ampoule 14 and the substrate 16 naturally flows into the enzyme-gel matrix when the ampoule 14 is crushed. However, the enzyme-gel matrix 18 may also be coated anywhere on the interior walls of the outer container 12.

Figure 3:
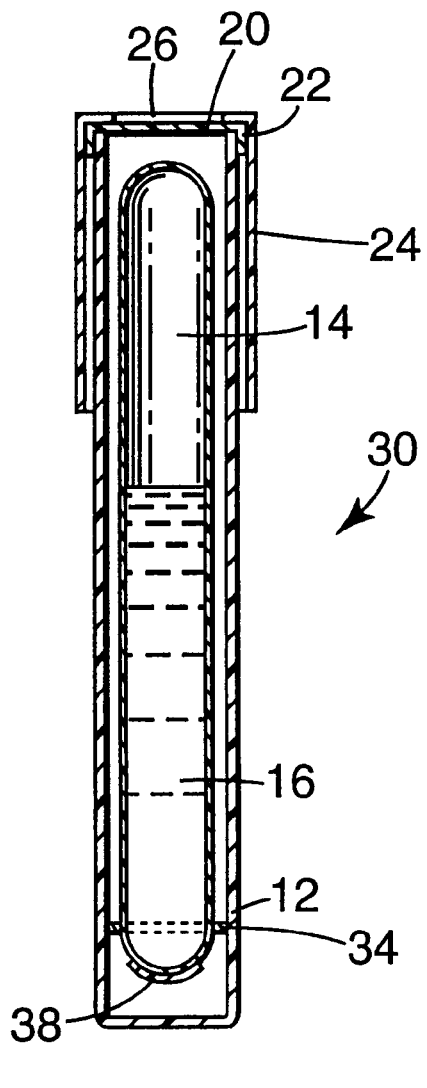
FIG. 3 is a cross-sectional view of an alternative embodiment of the sterilization indicator of the invention.

FIG. 3 illustrates an alternative embodiment of the indicator 30 in which the enzyme-gel matrix 38 is coated onto the exterior surface of the ampoule 13, near the end of the ampoule that faces the closed end of the outer container 12. In this embodiment, a partial barrier 34 is affixed to the interior wall of the outer tube 12. The barrier 34 suspends the ampoule 14 above the closed end of the outer container 12 and thereby prevents the enzyme-gel matrix 38 from being removed or displaced through contact with the surface of the outer container 12.

Figure 4:
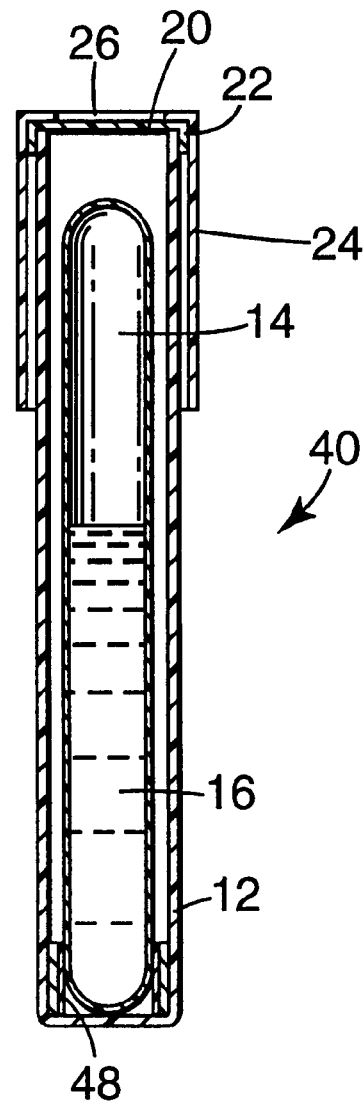
FIG. 4 is a cross-sectional view of an alternative embodiment of the sterilization indicator of the invention.

FIG. 4 illustrates an embodiment of the indicator 40 in which the enzyme-gel matrix is coated on a carrier strip 48, such as a strip of filter paper or some other substrate, placed in the bottom of the outer tube 12. The carrier strip 48 is made of a material that is not degraded or destroyed by contact with a liquid sterilant, and is preferably absorbent. The carrier strip 48 may be made of any of the materials that are suitable for use in making the cover membrane 22.

FIG. 5 illustrates an embodiment of the indicator 50 in which the enzyme-gel matrix 58 is coated on an exterior side wall of the ampoule 14.

FIG. 6 illustrates an embodiment of the indicator 60 that is identical to the indicator in FIG. 4, except that indicator 60 lacks a partial barrier to keep the enzyme-matrix 68 from contacting the surface of outer container 12.

Figures 7, 8:
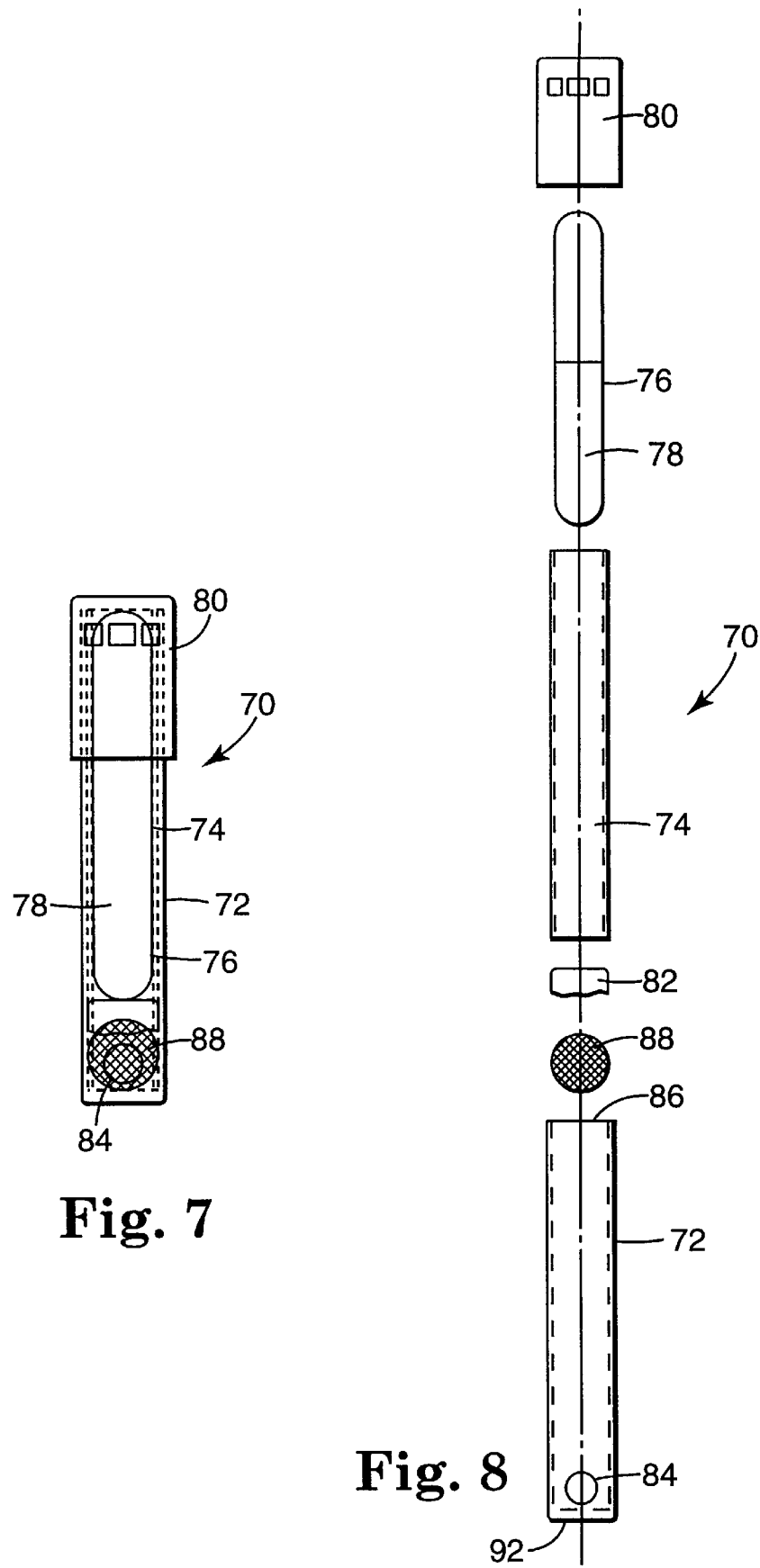
FIG. 7 is a cross-sectional view of an alternative embodiment of the sterilization indicator of the invention.
FIG. 8 is an exploded view of the indicator shown in FIG. 7.

FIGS. 7–8 illustrate an alternative embodiment of the indicator 70 in which the enzyme-gel matrix is coated on a glass bead. The indicator 70 includes an outer sleeve 72 having an open end 86, a closed end 92 and a sterilant portal 84 proximate the closed end 92. A glass bead 88 coated with enzyme-gel matrix is disposed near the closed end 92 of the outer sleeve, facing the sterilant portal 84 and in fluid communication with the exterior of the tube through the portal. A barrier 82 separates the glass bead from an inner sleeve 74, which has a diameter slightly greater than that of the glass bead 88 and which is adapted so that it can be slid over bead 88. The inner sleeve 74 contains an ampoule 76 containing a substrate solution 78, and preferably growth medium. Cap 80 fits snugly over the outer diameter of outer tube 72 and holds the components of the indicator 70 together.

During a sterilization procedure, liquid sterilant enters the indicator 70 through sterilant portal 84 and contacts the enzyme-gel matrix on bead 88. The cap 80 is then pressed downward, crushing the ampoule 76 and at the same time sliding the inner sleeve 74 over the glass bead 88 until it reaches the closed end 92 of the tube, blocking sterilant portal 84 so that liquid cannot escape. Substrate solution 76 passes through and around barrier 82 and contacts the source of active enzyme on glass bead 88. The indicator is then incubated for a period of time necessary for the substrate to react with any remaining active enzyme and provide a detectable signal indicating that the sterilization procedure has failed. If the indicator is a dual rapid readout indicator, the incubated for an additional period of time necessary for any surviving spores to grow out.

The outer sleeve 72, inner sleeve 74, and cap 80 may be made of the same materials as described above for use in constructing the outer container of the indicators shown in FIGS. 1–6. The barrier material 82 is preferably made of a nonwoven polymeric material, and most preferably of polypropylene blown microfiber material, commercially available as THINSULATE™ brand Thermal Insulation from 3M Company, St. Paul, Minn. The glass bead 84 may be of any size. In a preferred embodiment, the bead is about 6 mm in diameter. In addition, it is conceivable that 2 or more coated glass beads may be used, instead of one, and all such variations and considered to be within the scope of the invention.

The indicators of the invention may be used to monitor any sterilization procedure that sterilizes articles by contacting them with a liquid sterilant. For example, the indicators are suitable for use with liquid sterilant procedures that use liquid peracetic acid; active chlorine compounds, such as elemental chlorine, calcium hypochlorite, potassium hypochlorite, chlorinated trisodium phosphate, chorine dioxide decahydrate, chlorine dioxide, hypochlorous acid, hypochlorite ions, inorganic chloramines, and organic chloramines; active iodine compounds; active bromine compounds; hydrogen peroxide; aldehydes, such as glutaraldehyde, formaldehyde, glyoxal, malonaldehyde, succinaldehyde, adipaldehyde; and phenolic compounds.

The operation of the present invention will be further described with regard to the following detailed example. The examples is offered to further illustrate the various specific and preferred embodiments and techniques. It should be understood, however, that many variations and modifications may be made while remaining within the scope of the present invention.

EXAMPLE 1

This example demonstrates that rapid readout sterilization indicators made with spores suspended in a gel matrix provide accurate results when used to monitor the effectiveness of a liquid peracetic acid sterilization procedure.

Glass beads coated with *Bacillus stearothermpohilus* spores dispersed within a gel were exposed to a sterilization procedure in a STERIS SYSTEM™ liquid peracetic acid sterilizer. The beads were then incubated in a solution containing a substrate that reacts with an enzyme expressed by the spores and a growth medium that stimulates the growth of live spores, and examined for fluorescence indicating an enzyme reaction and spore growth.

The spore-gel material used to coat the glass beads was prepared by adding cultured spores to a polymeric gel of polyvinylpyrolidone/polycarbamyl polyglycol ester. *Bacillus stearothermpophilus*, commercially available as ATCC 7953 from American Type Culture Collection, Rockville, Md., was grown overnight or for about 16 hours at 58° C. in tryptic soy broth. This culture was used to inoculate the surface of agar plates consisting of 8 g/l nutrient broth, 4 g/l yeast extract, 0.1 g/l manganese chloride and 20 g/l agar at pH 7.2. Plates were incubated at 58° C. for 72 hours. Spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. The cleaning procedure was repeated several times.

After the final wash, the supernatant was poured off and the spores were suspended in PECOGEL™ H-1220 polyvinylpyrolidone/polycarbamyl polyglycol ester, diluted 1:8 in water, obtained from Phoenix Chemical, Somerville, N.J., at a concentration of approximately $1\times10^8$ spores per milliliter. 50 microliters of spore-gel suspension containing approximately $5\times10^6$ spores were coated on 6 mm sterile glass beads, obtained from 3M Company, St. Paul, Minn.

The coated beads were placed in a perforated container and exposed to a liquid peracetic acid sterilization procedure in a STERIS SYSTEM™ sterilizer, obtained from Steris Corporation, Mentor, Ohio. The beads were sealed in the sterilizer and exposed to a preliminary wash with an anti-corrosive buffer solution. 60 milliliters of 35% liquid peracetic acid was then introduced to the buffer solution and circulated throughout the sterilization chamber for 12 minutes at 50–56° C. The circulating sterilant had a liquid peracetic acid concentration of 0.2% and a pH of 6.4. The sterilant was then drained and the sterilizing chamber was washed with water four times.

The sterilized beads were then used to make a sterilization indicator as shown in FIGS. 1–2. The beads were aseptically transferred into an outer tube 12 in FIGS. 1–2, and a barrier material was placed over the beads. A glass ampoule 14 containing enzyme substrate and spore growth medium was placed above the barrier material. A closure member 22 and cap 24 were placed over the end of the tube. A 1.75 mm disc of polypropylene blown microfiber material, with a weight of 200 g/m$^2$, commercially available as "THINSULATE"™ 200-B brand Thermal Insulation from 3M Company, St. Paul, Minn., was used as the barrier material. The ampoule 14 contained 0.67 ml nutrient medium, consisting of 17 g of a bacteriological peptone and 0.17 g/l of L-alanine, as well as 0.1 g 4-methylumbelliferyl-alpha-D-glucoside, commercially available from Sigma Chemical Company, St. Louis, Mo., dissolved in 200 microliters of N,N-demethylformamide, and 0.03 g bromocresal purple pH indicator dye, per liter of water. The pH of the enzyme substrate and nutrient medium solution was adjusted to 7.6 with 0.1N sodium hydroxide.

The outer container 12 and the cap 24 were both made of polypropylene. The outer container was 5.08 cm long with an outer diameter of 85.1 mm and an internal diameter of 77.0 mm. The cap 24 was 1.275 cm long with an internal diameter of 83.3 mm. The ampoule was made of glass and was 3.96 cm long, with an outer diameter of 65.5 mm and a wall thickness of 2.5 mm. The closure member 22 was a piece of sterilization grade filter paper have a diameter of 1.27 mm.

After assembly of the indicators the ampoules were crushed and the indicators were incubated at 60° C. The indicators were examined for fluorescence using a 3M™ ATTEST™ Model 190 Rapid Autoreader, commercially available from 3M Company, St. Paul, Minn. Additionally, spore growth, as indicated by a color change from purple to yellow, was determined visually.

The number of growth positive indicators detected after 168 hr is recorded in Table 1. The percentages of these growth positive indicators that also demonstrated fluorescence at 6 hr and 8 hr are also recorded in Table 1. For purposes of judging the accuracy of the sterilization indicators in Table 1, a fluorescent positive percentage of 100% is perfect, indicating that all the growth positives were detected as fluorescent positives and no false negatives were detected. A fluorescent positive number of less than 100%, on the other hand, indicates that there were one or more false negatives, in that some of the indicators that were negative for fluorescence were later detected as positive for spore growth.

The data in Table 1 indicate that there was 100% agreement between the fluorescence and spore outgrowth results for all samples tested, supporting the conclusion that gels of polyvinylpyrolidone/polycarbamyl polyglycol esters are highly effective as carrier materials for spores in rapid readout sterilization indicators.

TABLE 1

| GEL | TOTAL UNITS TESTED | NO. GROWTH POSITIVE 168 HR | FLUORESCENCE 6 HR | 8 HR |
|---|---|---|---|---|
| Polyvinyl pyrolidone/polycarbamyl polyglycol ester | 390 | 261 | 100% | 100% |

What is claimed is:

1. A sterilization indicator for testing the effectiveness of a sterilization procedure that disinfects objects by contacting them with a liquid sterilant, comprising:
    (a) an outer container having one open end, the outer container being constructed of a compressible plastic material that is impermeable to liquids and bacteria;
    (b) a cover membrane associated with the open end of the outer container, the cover membrane being permeable to liquids but impermeable to bacteria;
    (c) an enzyme-gel matrix coated on a surface within the outer container comprising a water-insoluble, biologically inert polymeric gel and a source of an active enzyme dispersed within the gel, wherein the enzyme-gel matrix is selected such that during the sterilization procedure the liquid sterilant may enter the matrix and contact the source of active enzyme without substantially washing the source of enzyme out of the indicator, wherein the enzyme has an enzyme activity that is correlated with the survival of at least one test microorganism commonly used to monitor the effectiveness of a sterilization procedure, and wherein the enzyme is substantially inactivated by a sterilization procedure that is lethal to the test microorganism but is not substantially inactivated by a sterilization procedure that is not lethal to the test microorganism;
    (d) a breakable ampoule within the outer container, the ampoule being impermeable to the sterilant used in the sterilization procedure; and
    (e) a substrate within the ampoule, the ampoule being adapted so that it may be crushed after a sterilization procedure, by compressing the outer container, to release the substrate and bring it into contact with the source of active enzyme, wherein the substrate is capable of reacting with any active enzyme remaining after the indicator has been subjected to a sterilization procedure to provide a detectable indication that the sterilization procedure was ineffective;
    wherein the polymeric gel comprises a gel selected from the group consisting of: a polyvinylpyrolidone/polycarbamyl polyglycol ester; a polyvinylpyrolidone/dimethylaminoethylmethacrylate/polycarbamyl polyglycol ester; and a polyvinylpyrolidone/dimethiconylacrylate/polycarbamyl polyglycol ester.

2. A sterilization indicator for testing the effectiveness of a sterilization procedure that disinfects objects by contacting them with liquid peracetic acid sterilant, comprising:
    (a) an outer container having one open end, the outer container being constructed of a compressible plastic material that is impermeable to liquids and bacteria;
    (b) a cover membrane associated with the open end of the outer container, the cover membrane being permeable to liquids but impermeable to bacteria;
    (c) an enzyme-gel matrix coated on a surface within the outer container comprising a water-insoluble, biologically inert polymeric gel and a source of an active enzyme dispersed within the gel, wherein the enzyme-gel matrix is selected such that during the sterilization procedure the liquid sterilant may enter the matrix and contact the source of active enzyme without substantially washing the source of enzyme out of the indicator, wherein the enzyme has an enzyme activity that is correlated with the survival of at least one test microorganism commonly used to monitor the effectiveness of a sterilization procedure, and wherein the enzyme is substantially inactivated by a sterilization procedure that is lethal to the test microorganism but is not substantially inactivated by a sterilization procedure that is not lethal to the test microorganism;
    (d) a breakable ampoule within the outer container, the ampoule being impermeable to liquid peracetic acid sterilant; and
    (e) a substrate within the ampoule, the ampoule being adapted so that it may be crushed after a sterilization procedure, by compressing the outer container, to release the substrate and bring it into contact with the source of active enzyme, wherein the substrate is capable of reacting with any active enzyme remaining after the indicator has been subjected to a sterilization procedure to provide a detectable indication that the sterilization procedure was ineffective;
    wherein the polymeric gel comprises a gel selected from the group consisting of: a polyvinylpyrolidone/polycarbamyl polyglycol ester; a polyvinylpyrolidone/dimethylaminoethylmethacrylate/polycarbamyl polyglycol ester; and a polyvinylpyrolidone/dimethiconylacrylate/polycarbamyl polyglycol ester.

3. A method of testing the effectiveness of a sterilization procedure that disinfects objects by contacting them with a liquid sterilant, comprising the steps of
    (a) providing a sterilization indicator comprising:
        (i) an outer container having one open end, the outer container being constructed of a compressible plastic material that is impermeable to liquids and bacteria;
        (ii) a cover membrane associated with the open end of the outer container, the cover membrane being permeable to liquids but impermeable to bacteria;
        (iii) an enzyme-gel matrix coated on a surface within the outer container comprising a water-insoluble, biologically inert polymeric gel and a source of an active enzyme dispersed within the gel, wherein the enzyme-gel matrix is selected such that during the sterilization procedure the liquid sterilant may enter the matrix and contact the source of active enzyme without substantially washing the source of enzyme out of the indicator, wherein the enzyme has an enzyme activity that is correlated with the survival of at least one test microorganism commonly used to monitor the effectiveness of a sterilization procedure, and wherein the enzyme is substantially inactivated by a sterilization procedure that is lethal to the test microorganism but is not substantially inactivated by a sterilization procedure that is not lethal to the test microorganism;

(iv) a breakable ampoule within the outer container, the ampoule being impermeable to the sterilant used in the sterilization procedure; and (v) a substrate within the ampoule, the ampoule being adapted so that it may be crushed after a sterilization procedure, by compressing the outer container, to release the substrate and bring it into contact with the source of active enzyme, wherein the substrate is capable of reacting with any active enzyme remaining after the indicator has been subjected to a sterilization procedure to provide a detectable indication that the sterilization procedure was ineffective:

(b) subjecting the sterilization indicator to a sterilization procedure that uses a liquid sterilant;

(c) incubating the sterilization indicator; and (d) examining the sterilization indicator for a detectable indication that the sterilization procedure was ineffective;

wherein the polymeric gel comprises a gel selected from the group consisting of: a polyvinylpyrolidone/polycarbamyl polyglycol ester; a polyvinylpyrolidone/ dimethylaminoethylmethacrylate/polycarbamyl polyglycol ester; and a polyvinylpyrolidone dimethiconylacrylate/ polycarbamyl polyglycol ester.

* * * * *

UNITED STATES PATENT AND TRADEMARK OFFICE
CERTIFICATE OF CORRECTION

PATENT NO. : 6,566,090 B2
DATED : May 20, 2003
INVENTOR(S) : Witcher, Kelvin J.

It is certified that error appears in the above-identified patent and that said Letters Patent is hereby corrected as shown below:

Column 2,
Line 26, delete the word "to" following the word "likely";
Line 31, replace the word "stearothermpophilus" with -- stearothermophilus --;

Column 7,
Line 21, replace the word "microorganism" with -- microorganisms --;

Column 8,
Line 59, delete "12" and insert in place thereof -- 22 --;

Column 9,
Line 9, insert the word -- more -- preceding the word "members";
Line 31, replace the word "used" with -- use -- ;
Line 38, replace the word "hydroxmethylacrylate" with -- hydroxymethylacrylate --;
Line 54, replace the word "PEGOGEL" with -- PECOGEL --;

Column 10,
Line 4, delete "$10^2 1410^8$" and insert in place thereof -- $10^2 - 10^8$ --;
Line 19, replace the word "shows" with -- show -- ;
Line 23, delete the word "solution" and insert in place thereof -- substrate --;

Column 11,
Line 27, delete the word "and" and insert in place thereof -- are --;
Line 35, replace the word "chorine" with -- chlorine --.

Signed and Sealed this

Thirtieth Day of December, 2003

JAMES E. ROGAN
*Director of the United States Patent and Trademark Office*